United States Patent
Marotta et al.

(10) Patent No.: US 6,905,696 B2
(45) Date of Patent: Jun. 14, 2005

(54) ALIGNMENT OF ENHANCERS IN COSMETIC COMPOSITIONS

(75) Inventors: Paul H. Marotta, Farmingdale, NY (US); John R. Castro, Huntington Station, NY (US); Carl C. Orr, Scotch Plains, NJ (US); Helen Sung, Brooklyn, NY (US); David Peters, Amityville, NY (US)

(73) Assignee: Color Access, Inc., Melville, NY (US)

( * ) Notice: Subject to any disclaimer, the term of this patent is extended or adjusted under 35 U.S.C. 154(b) by 25 days.

(21) Appl. No.: 10/336,903

(22) Filed: Jan. 6, 2003

(65) Prior Publication Data

US 2004/0131649 A1 Jul. 8, 2004

(51) Int. Cl.$^7$ .................................................. A61K 7/00
(52) U.S. Cl. ...................... 424/401; 424/70.6; 424/70.7
(58) Field of Search ................ 424/401, 70.6, 424/70.7

(56) References Cited

U.S. PATENT DOCUMENTS

| | | | |
|---|---|---|---|
| 3,950,510 A | * | 4/1976 | Adams .................. 424/70.22 |
| 3,964,500 A | | 6/1976 | Drakoff .................. 132/7 |
| 4,820,510 A | | 4/1989 | Arraudeau et al. .......... 424/63 |
| 5,662,891 A | * | 9/1997 | Martin .................... 424/61 |
| 5,747,058 A | | 5/1998 | Tipton et al. .............. 424/423 |
| 5,965,146 A | * | 10/1999 | Franzke et al. ............ 424/401 |
| 6,306,407 B1 | | 10/2001 | Castro et al. ............. 424/401 |

FOREIGN PATENT DOCUMENTS

| | | |
|---|---|---|
| JP | 03-153613 | 7/1991 |
| JP | 7-179323 | 7/1995 |

OTHER PUBLICATIONS

Product Literature for Eastman Chemical Co., Kingsport, TN (Oct., 1999).

* cited by examiner

*Primary Examiner*—Gary Kunz
*Assistant Examiner*—Konata M. George
(74) *Attorney, Agent, or Firm*—Dorene M. Price

(57) ABSTRACT

The present invention relates to a cosmetic or pharmaceutical composition for topical application to the keratinous surface which comprises a alignment agent for promoting the orderly arrangement of a feature enhancing component for enhancing the lengthening of the eyelashes and/or the covering of wrinkles on the skin surface. The feature enhancing component can be a fibrous component and can include a variety of types of fibers including wicking fibers, evaporating fibers, or a combination of both. The feature enhancing component can also be inert fillers such as platelet materials.

13 Claims, No Drawings

ALIGNMENT OF ENHANCERS IN COSMETIC COMPOSITIONS

FIELD OF THE INVENTION

The invention relates to cosmetic or pharmaceutical compositions. More specifically, the invention relates to such compositions having an alignment agent capable of arranging a feature enhancing component on the keratinous surface to mimic the desired enhancement of the keratinous surface.

BACKGROUND OF THE INVENTION

Although beauty is in the eye of the beholder, broadly speaking, certain facial features are considered to embue beauty. The ability of cosmetics and skin care products to enhance these features, and therefore, one's beauty, is the cornerstone of an industry that offers these products. Examples of features that can be enhanced for a dramatic beautiful look include, the eyes, the skin tone, and the lips. However, one common beauty detractor that affects each of these examples are wrinkles. Thus, many products are designed to prevent, hide or cover the unsightly wrinkle. Other cosmetic products rather than address what may be considered a flaw, take an otherwise, natural feature and make it look even better. This is true of mascara compositions which transform the natural eyelash into a rich voluminous enhancement to the eye.

Long and thick eyelashes are considered to be an attractive enhancement to the eye area. They create a dramatic look that is appealing to many. Thus, mascara users desire lashes that look long, luscious, full, soft, and separated. However, many "volumizing" mascaras are messy, clumpy, and leave thin lashes looking stiff, harsh and quite noticeable but in an unattractive way. These types of mascaras may also feel heavy on the lashes when applied. Another challenge with using mascaras that volumize is that they can tend to smear, smudge or flake off. Cosmetic products no matter how they are designed to enhance beauty, must also withstand the build up of moisture and oily residue. To achieve a product for topical application on the skin it is desirable that the product be light, refreshing and natural feeling but, also it must continue to enhance beauty as it did when it was initially applied by managing the moisture and oil on the skin. Therefore, the product must be formulated to look good on the skin or hair, and perform its desired function. Thus, there remains a need to enhance features on the skin or hair, without the unwanted characteristics associated with current products. The present invention achieves these goals and meets the need enhancing features associated with beauty under circumstances of normal daily use.

SUMMARY OF THE INVENTION

The present invention relates to a cosmetic or pharmaceutical composition for topical application to a keratinous surface which comprises a feature enhancing component and a non-polymeric alignment agent for promoting the orderly arrangement of the feature enhancing component on the keratinous surface. The feature enhancing component is aligned on the keratinous surface to lengthen the eyelashes or cover the wrinkles on the lips or skin. The feature enhancing component may be a fibrous component comprising fibers that align on the hair, lips or the skin. In addition, the fibrous component may also comprise inert fillers such as platelets that can cover wrinkles on the skin. The feature enhancing component is therefore, either fibers or platelets, or both fibers and platelets. If both fibers and platelets are used, the feature enhancing component performs two basic functions in that the skin tone appears natural and less wrinkled because first, wrinkles on the surface of the skin are covered; and second, fibers mimic the natural look of the skin. The compositions of the present invention are particularly useful as a mascara.

The present invention also includes a method of enhancing the keratinous surface. The feature enhancing component is combined with the alignment agent and applied to the skin. The compositions of the present invention enhance the keratinous surface by arranging the feature enhancing component on the keratinous surface. As a result, the appearance of wrinkles on the skin can be reduced and the skin has a more natural appearance. The fibers are also particularly useful in a mascara composition whereby, upon application to the eyelashes, lengthening enhancement is achieved on the keratinous surface by the methodic ordering of the fibers on the lashes when the non-polymeric alignment agent is sucrose acetate isobutyrate.

DETAILED DESCRIPTION OF THE INVENTION

The present invention relates to a cosmetic or pharmaceutical composition for topical application to a keratinous surface which comprises a feature enhancing component and a non-polymeric alignment agent for promoting the orderly arrangement of the feature enhancing component on the keratinous surface. The feature enhancing component is aligned on the keratinous surface to, for example, lengthen the eyelashes or cover the wrinkles on the lips or skin. The feature enhancing component may be a fibrous component comprising fibers which align on the hair or the skin. In addition, the fibrous component may comprise fillers such as platelets that cover wrinkles on the skin or the lips. The feature enhancing component can therefore, be either fibers or platelets, or both fibers and platelets. If both fibers and platelets are used, the feature enhancing component performs two basic functions such that the skin appears natural and less wrinkled. First, it covers wrinkles on the surface of the skin and second, the fibers mimic the natural look of the skin. The feature enhancing component of the present invention is not randomly applied on the keratinous surface. Rather, the alignment agent arranges the feature enhancing component on the keratinous surface in an orderly fashion.

The alignment agent is a non-polymeric, non-water soluble highly viscous liquid material. The viscosity of the alignment agent is at least about 5,000 centipoise, and preferably at least about 20,000 centipoise, and more preferably at least about 50,000 all at about 37° C. Preferably, the alignment agent is sucrose acetate isobutyrate (SAIB), a sucrose molecule esterified with two acetic acid and six isobutyric acid moieties. The most common use of SAIB is as a plasticizer in nail enamel compositions as set forth, for example, in U.S. Pat. No. 5,662,891, as part of a drug delivery system as provided in U.S. Pat. No. 5,747,058, and in shampoo compositions as described in U.S. Pat. No. 3,964,500. In addition, SAIB is known to stabilize emulsions in the food industry as described in product literature for Eastman Chemical Co., Kingsport Tenn. (October, 1999). As a very viscous liquid, about 100,000 centipoise at about 30° C., SAIB has an unusual property of changing in viscosity with change in temperature or with the addition of solvents. For example, according to product literature on SAIB from Eastman Chemical Co., Kingsport Tenn. (October, 1999), an increase in temperature of only about 20° C. reduces its viscosity. SAIB is not miscible with glycerol, corn oil, peanut oil, 1,2-propanediol, polyethylene glycol, super refined sesame oil, and super refined peanut oil. Thus, these types of solvents are not preferred in the compositions of the present invention. Another desirable quality of SAIB is its tackiness as exemplified by its good adhesion to substrates, such as the skin and hair. The tackiness of SAIB can also be modified by the presence of other formulation ingredients. The alignment agent is present in an amount of about 0.2 to 20.0 percent by weight of the composition. In the mascara compositions, of the present invention, SAIB is present in an amount of about 0.5 to about 10 percent by weight of the composition.

Generally, in one embodiment of the present invention, the feature enhancing component is a fibrous component containing fibers to facilitate the lengthening of eyelashes or to mimic the natural fine hairs on the skin surface. The fibers are arranged in an linear order such that the fibers align on the lash to enhance the lengthening effect. The fibers are positioned, generally speaking, end to end so that they form a line of fibers and cause a lengthening effect on the lash. The fibers can be, for example, nylon, polyester, polypropylene, silk, cotton, wool, flax, cellulose, polyamide, viscose, acetate, acrylic polymer, aramid, rayon, polyolefin, glass, silica, carbon, polytetrafluoroethylene, insoluble collagen, polyester, polyvinyl chloride, polyvinylidene chloride, polyvinyl alcohol, polyacrylonitrile, chitosan, polyurethane, or polyethylene. The fiber can be in the form of flock having a length from about 0.01 to about 0.25 inches, however, the length can as long as about 30 mm.

The fibers of the feature enhancing component are hydrophobic and/or hydrophilic in nature. A combination of fibers can be used in the present invention. It is known to include fibers in cosmetic compositions in U.S. Pat. No. 4,820,510 and JP 7179323, and Japan Application No. 01291133. However, a cosmetic containing a non-polymeric aligning agent to methodically arrange fibers on the keratinous surface to lengthen the eyelashes has not been previously suggested. While certain fibers are inherently hydrophobic, the fibers can also be treated to be substantially hydrophobic. The term "substantially hydrophobic" means the fiber is lipophilic, oil-attracting and has a greater affinity for non-polar substances such as sebum, fatty acids, esters and other oils found on the skin than it does for other polar substances such as water. Fibers treated to be hydrophobic are usually treated chemically. Likewise, fibers can be treated to be hydrophilic, and the term "substantially hydrophilic" means that the fiber is attracted to water and has a greater affinity for water than it does for oil.

The hydrophobic fibers can be selected from the group consisting of nylon, polyester, polypropylene materials, and blends thereof. Other hydrophobic fibers, such as polyester may be used as, for example fibers under the tradenames COOLMAX™ and THERMAX™ which are manufactured by DuPont of Wilmington, Del. In a more preferred embodiment of the present invention, the fibrous component comprises hydrophobic fibers of nylon fibers. Nylon is inherently hydrophobic, however, it also absorbs water by the capillary type of action and has a dual affinity. The nylon has a denier (dpf) from about 0.8 to about 20, and preferably it can be about 1.0 to about 5.0. The nylon fibers can also be microdenier. The moisture regain of the nylon fiber is from about 4.0 to about 4.5 percent at about 70° F. and about 65 percent relative humidity. Higher temperatures and lower levels of humidity may enhance the performance of the composition. Preferably, the nylon fibers are fibers of nylon-6. The shape of the fibers can be any assortment of shapes such as round, bean, bone, oval, trilobal, irregular, or other fiber like shapes. Preferably the fibers are round.

Examples of fibers that are hydrophilic or treated to be substantially hydrophilic include but are not limited to polyethylene, polypropylene, acrylic, aramid, rayon, cotton, wool, silk and blends thereof. An example of treated hydrophilic nylon fibers are Intera-treated nylon fibers processed by the Intera Corporation of Cleveland, Tenn., and nylon 6 copolymer under the tradename HYDROFIL™ manufactured by Allied Signal Fibers of Petersburg, Va. Other similarly treated fabrics such as a modified polyester under the tradename THERMASTAT™, manufactured by DuPont of Wilmington, Del., and a modified acrylic under the tradename DUNOVA™, manufactured by Bayer of Leverkusen of Germany are available. Other manufacturers of fabrics can be used as well.

In yet another embodiment of the present invention, the cosmetic or pharmaceutical composition comprises a combination of fibers and platelets (i.e., the two feature enhancing components are present in the composition together). The combination of these two feature enhancing components arranged in a methodical order work synergistically together to provide combined benefits. The platelets assist the fibers in achieving lengthening and thickening of the lashes when applied as a mascara. Alternatively, when combined in a general cosmetic or skin care product, the skin has a natural look due to the presence of the fibers, but in addition to that, the platelets promote the coverage of wrinkles. The fibers also provide an addition benefit in that moisture can be evaporated because the fibers are oriented in a natural manner that allows air to pass through. The skin feels more comfortable when moisture is no longer settled on the surface of the skin. Further, still if the fibers are hydrophobic they may wick oil off of the skin surface. While, fibers that are hydrophilic are capable of evaporating moisture from the skin surface. Fibers such as these are described in U.S. Pat. No. 6,306,407.

The fibrous component is present in an amount sufficient to be arranged in order by the aligning agent without appearing fuzzy on the surface of the skin when applied. A sufficient amount of fiber also gives the composition a natural look on the skin similar to that of the natural ultrafine hairs that exist on the surface of the skin. The fibrous component is present in an amount of from about 0.01 to about 5.0 percent by weight by weight of the composition, preferably it is present in an amount of from about 0.05 to about 1.0 percent by weight of the composition. The amount of fibers when applied to the eyelashes is preferably, about 0.2 to about 2.0 percent by weight of the composition.

As mentioned the fibers can be in combination with a platelet. In addition, the compositions of the present invention can contain the platelet by itself as the feature enhancing component. The platelets in combination with the alignment agent achieve a lengthening and/or thickening effect on the lashes or an enhanced coverage of wrinkles on the skin surface. The platelet similar to the fiber is aligned end to end, but in a two dimensional fashion to achieve an enhanced coverage of wrinkles on the skin surface. The platelet can be, for example, mica, bismuth oxychloride, sericite, alumina, aluminum, copper, bronze, silver or silica. Examples of available platelets with soft focus materials incorporated include products available from Ikeda (Velvetveil) a mica coated with spherical silica beads, (Soft Vision) a mica coated with silica beads and further coated with $TiO_2$, (Ganzpearls GSC-30SR, and GSC-30MC) a sericite and crosslinked polystyrene, and a mica and crosslinked polystyrene, respectively. The alumina platelet can be treated with iron oxide and is available commercially from Cardre Inc., South Plainfield, N.J., as Pearl Copper 1000. It is a brown lustrous powder (similar to a rubbed penny) and has a particle size of about 10 to about 20 microns, preferably about 14 to 18 microns. The platelet is present in a total amount of about 0.1 to about 10.0 percent, preferably about 0.2 to about 5.0 percent. When the platelet is Soft Vision the haze is about 70 to 90 percent (ratio of diffused light to total transmission of light), total transmission of light is about 60 to 80 percent, and the haze is greater than the total transmission of light.

The composition also includes a compatible carrier. By "compatible carrier" in the present specification and claims is meant any cosmetically acceptable carrier which is compatible with the aligning agent. The carrier may contain one or more oil components. The oil component may be any pharmaceutically or cosmetically acceptable material which is substantially insoluble in water. These materials can be found for example in the CTFA International Dictionary of Cosmetic Ingredients as well as the U.S. Pharmacopocia or other equivalent sources. Suitable oil components include, but are not limited to, natural oils, such as coconut oil; hydrocarbons, such as mineral oil and hydrogenated polyisobutene; fatty alcohols, such as octyldodecanol; esters, such as C12–15 alkyl benzoate; diesters, such as propylene glycol dipelargonate; triesters, such as glyceryl trioctanoate; sterol derivatives, such as lanolin; animal waxes, such as beeswax; plant waxes, such as carnauba; mineral waxes, such as ozokerite; petroleum waxes, such as paraffin wax; synthetic waxes, such as polyethylene; and mixtures thereof.

Suitable oil components may also be silicones. The silicone oil can be volatile or semi-volatile, or any combination thereof. Suitable volatile oils include cyclic and linear silicones, such as hexamethylcyclotrisiloxane, octamethylcyclotetrasiloxane, and decamethylcyclopentasiloxane or volatile linear dimethylpolysiloxanes; or mixtures thereof. Other volatile silicones include, but are not limited to, cyclomethicone; polymeric silicones such as dimethicone; alkylated derivatives of polymeric silicones, such as cetyl dimethicone and lauryl trimethicone; hydroxylated derivatives of polymeric silicones, such as dimethiconol; and mixtures thereof. The carrier comprises, in the composition as a whole, preferably silicone oil which is present in an amount of at least about 0.5 to about 60 percent by weight. Preferably, the compatible carrier is one that enhances the soft powdery feel of the composition. A particularly preferred carrier is a low volatile silicone oil.

The composition of the present invention includes one or more film-forming agents. The use of a film-former can also improve the wear of the composition, and can confer transfer-resistance to the makeup product. Examples of useful film-forming agents include natural waxes, polymers such as polyethylene polymers and copolymers of PVP, dimethicone gum, and resins, such as shellac, polyterpenes, and various silicone resins. Preferably, the film-former is used in an amount of from about 0.1 to about 20 percent by weight of the total composition.

The composition of the present invention can also include polyurethane and derivatives thereof as, for example, trimethylol crosslinked polyurethane. While the compositions have a soft powdery feel due to the fiber content, the presence of polyurethane also contributes to the dry and powdery feel. Polyurethane is a slip agent which makes it easier to apply the composition to the skin. Therefore, the composition applies smoothly to the skin without the need to add oil and yet, does not drag or cake on the skin.

The present invention also includes a method of aligning the feature enhancing component on the keratinous surface by applying the compositions of the present invention containing the alignment agent to the skin. The compositions enhance the keratinous surface by reducing the appearance of wrinkles on the skin and leaving the skin with a natural appearance. The feature enhancing component is also particularly useful in a mascara composition when it solely contains fibers whereby, upon application to the eyelashes, the length of the eyelashes are enhanced by the methodical ordering of the fibers on the lashes. The orderly arrangement of the fibers on the lashes is particularly enhanced due to the presence of the SAIB as the alignment agent.

The benefit of the present cosmetic or pharmaceutical compositions can be obtained in any type of makeup composition, for example, mascaras, foundations, lipsticks and lipglosses. In a preferred embodiment, the compositions of the present invention are used in a mascara. In another embodiment of the present invention, the composition is a foundation or a lipstick comprising a fibrous component in which case, it may also be desirable to incorporate one or more waxes in the composition. The term "wax" will be understood to encompass not only waxes in the traditional sense, i.e., those plant, animal or mineral waxes containing primarily esters of higher fatty acids and alcohols, free higher acids and alcohols, and saturated hydrocarbons, but also synthetic resinous products having a wax-like, i.e., hard, brittle, relatively non-greasy texture at room temperature, such as silicone waxes. Examples of suitable waxes include, but are not limited to, carnauba wax, candelilla wax, beeswax, microcrystalline wax, polyethylene, japan wax, synthetic wax, shellac wax, spermaceti, lanolin wax, ozokerite, bran wax, ceresin wax, bayberry wax, paraffin, rice wax, mink wax, montan wax, ouricoury wax, jojoba wax, and the like.

Additional preferred components of the cosmetic compositions of the invention include one or more pigments. Any cosmetically acceptable pigment, either organic, inorganic, or combinations thereof, can be used in the makeup compositions of the invention. Examples of useful inorganic pigments include iron oxides (yellow, red, brown or black), ultramarines, chromium hydroxide green, chromium oxide, titanium dioxide (white), ferric ferrocyanide, ferric ammonium ferrocyanide, and mixtures thereof.

The organic pigments include natural colorants and synthetic monomeric and polymeric colorants. Exemplary are aromatic compounds such as azo, triphenylmethane, indigo, anthraquinone, and xanthine dyes, which are referred to as D&C or FD&C pigments. Also useful are lakes, which are pigments formed by the precipitation and absorption of organic dyes on an insoluble base, such as alumina, barium, or calcium hydrates. Particularly preferred lakes are primary FD&C or D&C lakes and blends thereof. In a preferred embodiment the pigment employed is hydrophobically treated. Such treatment assists in preventing oil breakthrough, and further aids in keeping the color true. Examples of useful hydrophobic surface treatments include but are not limited to amino acids, silicones, methicones, dimethicones, silanes, polyethylene, metal soaps, lecithin, waxes, nylon, or flourochemicals. Pigment concentrations will vary depending upon the color of the final product, but generally will be in the range of from about 5.0 to about 20 percent by weight of the total composition. Further, the fibers themselves can be pigmented.

The pigments can also be spherical scattering agents such as spherical powders that achieve a soft focus look. Examples, include but are not limited to, calcium aluminum borosilicate, PMMA, polyethylene, polystyrene, methyl methacrylate crosspolymer, nylon-12, ethylene/acrylic acid copolymer, boron nitride, Teflon, or silica. The composition can also contain small amounts of fillers or powders. Examples of such include silica, talc, mica, starch, nylon, kaolin, bismuth oxychloride, or coated versions of each of these, for example, with lecithin, silicones, amino acids, fatty acids, fatty alcohols, or metallic soap coatings. The addition of fillers or powders enhance the dry and powdery feel.

Another optional component of the composition is a metal stearate, where the metal is selected from the group consisting of zinc, calcium, copper, aluminum, lithium and magnesium. The presence of a metal stearate assists in the transfer resistance of the composition, and also improves the feel of the composition.

The composition can also contain other optional components including, but not limited to, oil soluble sunscreens, such as octyl methoxycinnamate; particulate sunscreens such as zinc oxide; oil-soluble antioxidants and/or preservatives, such as BHT; chelating agents such as Disodium EDTA; fragrances (such as pinene); flavoring agents; waterproofing agents (such as PVP/eicosene copolymer); surfactants, such as silicone copolyols or fatty acid glycerol esters; and oil-soluble actives, such as tocopherol and its derivatives or retinol and its derivatives; and the like.

The invention is further illustrated by the following non-limiting example.

EXAMPLES

I. Mascara Formulation

| Phase I | |
|---|---|
| Purified water | 20.0 |
| Nylon-6 | 0.3 |
| Titanium dioxide | 0.2 |
| Black iron oxide | 8.0 |
| Phase II | |
| Bentonite | 5.0 |
| Purified water | 25.0 |
| Butylene glycol | 1.5 |
| Parabens | 1.0 |
| Phase III | |
| Gyceryl stearate | 10.0 |
| Carnauba wax | 2.5 |
| Synthetic wax | 2.5 |
| Alignment agent | 3.0 |
| Phase IV | |
| Distilled Water | 4.0 |
| Polyvinyl alcohol | 1.0 |
| Acrylates copolymer | 5.0 |
| Ammonium acrylates copolymer | 10.0 |
| Butylene glycol | 1.0 |

The Phase I constituents of the above formula are mixed together using a high speed propeller mixer. After mixing, the Phase I constituents are combined with Phase II ingredients, mixed until Bentonite is fully dispersed, and heated to about 85° C. Phase III ingredients are added to the combined Phase I and II ingredients and cooled to about 60° C. Combine Phase IV ingredients with the combined Phase I, II, and III ingredients, mix, and cool down to about 32° C.

II. Measurement of Lengthening

A mascara containing fibers and the alignment agent, according to Example I of the present invention is prepared and a mascara without the fibers and the alignment agent is prepared by replacing them with water. Both mascaras are tested using a panel of 10 female individuals. Qualifying panelists are selected over the age of 18. They have medium eyelashes in length, e.g., about 0.6 to about 0.9 cm. Chosen panelists participate in a two day double blinded study and evaluations are carried out before application of the mascara for a baseline and immediately after application of the mascara. The panelists wear no makeup or moisturizer on the day of testing. Each panelist applies 40 strokes of the mascara to their upper lashes with one charged brush and 40 strokes to their lower lashes with a second charged brush. The mascara is charged onto the brush without pumping the brush in the mascara container. Images of the eyelashes are obtained using a Nikon Digital camera at a ration of 1:2.5. An image of each the right and left eye are recorded. The baseline image is used as a guideline for placement for the following visits to insure reproducibility. The images are digitized and analyzed to determine the "perceived eyelash length". An average of the length of five of the same eyelashes at each time point is made to determine the "perceived eyelash length." The results of the analysis demonstrate that the keratinous surface is enhanced by an increase of 41 percent over the baseline for the length of the lashes.

What we claim is:

1. A cosmetic or pharmaceutical composition for topical application to the eyelashes, lips and skin comprising a non-polymeric alignment agent comprising at least sucrose acetate isobutyrate and a feature enhancing component of fibers or platelets aligned on a keratinous surface for cosmetic enhancement.

2. The composition of claim 1 in which said alignment agent has a viscosity of at least about 5,000 centipoise at 37° C.

3. The composition of claim 1 in which said fibers are selected from the group consisting of nylon, polyester, polypropylene, silk, cotton, wool, flax, cellulose, polyamide, viscose, acetate, acrylic polymer, aramid, rayon, polyolefin, glass, silica, carbon, polytetrafluoroethylene, insoluble collagen, polyvinyl chloride, polyvinylidene chloride, polyvinyl alcohol, polyacrylonitrile, chitosan, polyurethane, polyethylene, and blends thereof.

4. The composition of claim 3 wherein said fibers are nylon.

5. The composition of claim 3 wherein said fibers further comprise fibers for evaporating moisture.

6. The composition of claim 1 which further comprises one or more pigments.

7. The composition of claim 1 which is a mascara or a foundation.

8. A mascara composition comprising a non-polymeric alignment agent comprising at least sucrose acetate isobutyrate, and a feature enhancing component comprising fibers aligned on a keratinous surface for lengthening enhancement.

9. The composition of claim 8 wherein said alignment agent is present in an amount of about 0.2 to 20.0 percent by weight of the composition.

10. The composition of claim 8 wherein said fibers are present from about 0.01 to about 5.0 percent by weight of the composition.

11. The composition of claim 8 which further comprises a film forming agent in an amount of from about 0.1 to about 20 percent by weight of the composition.

12. The composition of claim 10 which comprises one or more pigments in an amount of from about 0.1 to about 30 percent by weight.

13. A method of enhancing a keratinous surface of an eyelash, lip or skin comprising the steps of combining a feature enhancing component of fiber or platelet and a non-polymeric aligning agent comprising at least sucrose acetate isobutyrate, and arranging the feature enhancing component on the keratinous surface.

* * * * *